(12) United States Patent
Junio

(10) Patent No.: US 12,220,195 B2
(45) Date of Patent: Feb. 11, 2025

(54) SYSTEMS, METHODS, AND DEVICES FOR DEFINING A PATH FOR A ROBOTIC ARM

(71) Applicant: Mazor Robotics Ltd., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 530 days.

(21) Appl. No.: 17/500,559

(22) Filed: Oct. 13, 2021

(65) Prior Publication Data

US 2023/0113312 A1 Apr. 13, 2023

(51) Int. Cl.
  A61B 34/00 (2016.01)
  A61B 34/20 (2016.01)
  B25J 9/16 (2006.01)

(52) U.S. Cl.
  CPC .............. *A61B 34/70* (2016.02); *A61B 34/20* (2016.02); *B25J 9/1666* (2013.01); *B25J 9/1676* (2013.01); *A61B 2034/2065* (2016.02); *A61B 2034/2068* (2016.02)

(58) Field of Classification Search
  CPC . A61B 34/70; A61B 34/20; A61B 2034/2065; A61B 2034/2068; A61B 34/30; A61B 34/32; A61B 2034/2051; A61B 2034/2055; B25J 9/1666; B25J 9/1676
  See application file for complete search history.

(56) References Cited

U.S. PATENT DOCUMENTS

| | | | |
|---|---|---|---|
| 9,668,768 B2 | 6/2017 | Piron et al. | |
| 9,827,054 B2 | 11/2017 | Richmond et al. | |
| 10,531,926 B2 | 1/2020 | Roessler | |
| 2017/0333137 A1* | 11/2017 | Roessler | B25J 9/1676 |
| 2018/0333207 A1 | 11/2018 | Moctezuma De la Barrera | |

FOREIGN PATENT DOCUMENTS

WO  WO 2014/022786  2/2014

OTHER PUBLICATIONS

International Search Report and Written Opinion for International (PCT) Patent Application No. PCT/IL2022/051069, dated Feb. 13, 2023, 13 pages.

\* cited by examiner

*Primary Examiner* — Ian Jen
*Assistant Examiner* — Renee LaRose
(74) *Attorney, Agent, or Firm* — Sheridan Ross P.C.

(57) ABSTRACT

Systems, methods, and devices for defining a path for a robotic arm are provided. One or more no-fly zones may be generated. The one or more no-fly zones correspond to a section of a work volume defined as inaccessible to a robotic arm and the work volume is defined as accessible to the robotic arm. A pose of an object may be determined and an obstacles map based on the determined pose and known dimensions of the object may be generated. A path for the robotic arm may be defined that avoids collision with the object identified in the obstacles map and avoiding the one or more no-fly zones.

17 Claims, 3 Drawing Sheets

SYSTEMS, METHODS, AND DEVICES FOR DEFINING A PATH FOR A ROBOTIC ARM

BACKGROUND

The present disclosure is generally directed to path planning, and relates more particularly to defining a path for a robotic arm.

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

BRIEF SUMMARY

Example aspects of the present disclosure include:

A system for defining a path for a robotic arm according to at least one embodiment of the present disclosure comprises a robotic arm; an object; a processor; and a memory storing data for processing by the processor, the data, when processed, causing the processor to: generate one or more no-fly zones, wherein the one or more no-fly zones correspond to a section of a work volume defined as inaccessible to the robotic arm, wherein the work volume is defined as accessible to the robotic arm; determine a pose of the object; generate an obstacles map based on the determined pose and known dimensions of the object; and define a path for the robotic arm to orient along, the path avoiding collision with the object identified in the obstacles map and avoiding the one or more no-fly zones.

Any of the aspects herein, wherein the path orients the robotic arm to a surgical site on a patient.

Any of the aspects herein, further comprising a tool oriented by the robotic arm, and wherein the path orients the tool from a first position outside of a patient to a second position inside of a patient.

Any of the aspects herein, wherein the memory stores further data for processing by the processor that, when processed, causes the processor to: generate an alert when a distance between the robotic arm and the object reaches a threshold.

Any of the aspects herein, wherein the memory stores further data for processing by the processor that, when processed, causes the processor to: prevent forward movement of the robotic arm on the path when a distance between the robotic arm and one of the objects reaches a threshold.

Any of the aspects herein, wherein the object is positioned at least partially inside of a patient.

Any of the aspects herein, further comprising one or more markers disposed on the object.

Any of the aspects herein, wherein the one or more markers are at least one of infrared emitting devices, light emitting diodes, electromagnetic transmitters, radar repeaters, spheres, or reflective markers.

Any of the aspects herein, wherein determining the pose of the object comprises: receiving image data depicting the one or more markers; and determining a pose of the one or more markers based on the image data, the pose of the one or more markers correlating to the pose of the object.

Any of the aspects herein, further comprising a navigation system configured to track a pose of each of the one or more markers, and wherein determining the pose of the object uses the navigation system.

Any of the aspects herein, wherein generating the obstacles map comprises defining a three-dimensional boundary of the object based on the known dimensions of the object.

Any of the aspects herein, wherein the memory stores further data for processing by the processor that, when processed, causes the processor to: detect movement of the object; update a pose of the object in the obstacles map based on the detected movement; and update the path for the robotic arm based on the updated pose of object.

Any of the aspects herein, wherein generating the one or more no-fly zones comprises: scanning an operating room to determine one or more physical boundaries within the operating room; and defining the one or more no-fly zones based on the one or more physical boundaries.

A device for defining a path for a robotic arm according to at least one embodiment of the present disclosure comprises a processor; and a memory storing data for processing by the processor, the data, when processed, causing the processor to: generate one or more no-fly zones, wherein the one or more no-fly zones correspond to a section of a work volume defined as inaccessible to a robotic arm, wherein the work volume is defined as accessible to the robotic arm; determine a pose of object; generate an obstacles map based on the determined pose and known dimensions of the object; and define a path for the robotic arm to orient along, the path avoiding collision with the object identified in the obstacles map and avoiding the one or more no-fly zones.

Any of the aspects herein, wherein the memory stores further data for processing by the processor that, when processed, causes the processor to: generate an alert when a distance between the robotic arm and the object reaches a threshold.

Any of the aspects herein, wherein the memory stores further data for processing by the processor that, when processed, causes the processor to: prevent forward movement of the robotic arm on the path when a distance between the robotic arm and the object reaches a threshold.

Any of the aspects herein, wherein generating the obstacles map comprises defining a three-dimensional boundary of the object based on the known dimensions of the object.

Any of the aspects herein, wherein generating the one or more no-fly zones comprises: scanning an operating room to determine one or more physical boundaries within the operating room; and defining the one or more no-fly zones based on the one or more physical boundaries.

Any of the aspects herein, wherein determining the pose of the object comprises receiving image data depicting one or more markers disposed on the object and determining a pose of the one or more markers based on the image data, the pose of the one or more markers correlating to the pose of the object.

A system for defining a path for a robotic arm according to at least one embodiment of the present disclosure comprises a robotic arm; an object; one or more markers disposed on the object; a navigation system configured to track a pose of each of the one or more markers; a processor; and a memory storing data for processing by the processor, the data, when processed, causes the processor to: generate one or more no-fly zones, wherein the one or more no-fly zones correspond to a section of a work volume defined as inaccessible to the robotic arm, wherein the work volume is defined as accessible to the robotic arm; determine a pose of the one or more markers using the navigation system; generate an obstacles map based on the detected pose of the one or more markers and known dimensions of the object;

and define a path for the robotic arm to orient along, the path avoiding collision with the object identified in the obstacles map and avoiding the one or more no-fly zones.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
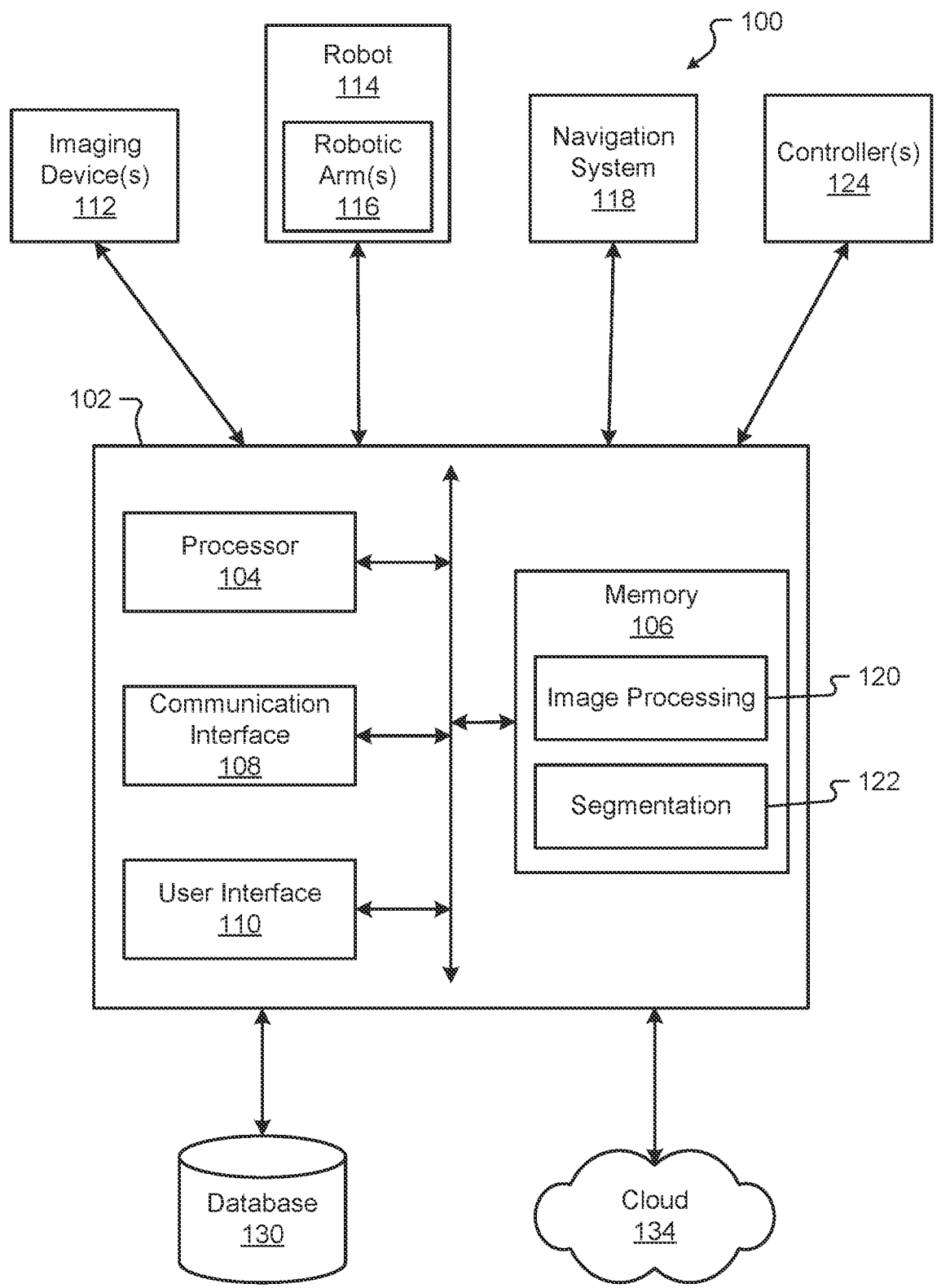
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

During a surgical operation, when autonomous robotic motion occurs within a patient anatomy (e.g., for bone cutting or screw insertion) a differentiation of the different materials that compose the surgical site is desirable (e.g., when aiming to cut tissue and bone, passing through the tissue and bone is acceptable, while passing through an instrument such as bone mount/retractors or other non-desired known materials/objects is not desired). Therefore, a positioning of those known instruments or objects is desired to assure correct autonomous path planning that avoids the known instruments or objects.

In at least one embodiment, navigation-detectable aids (e.g., spheres, electromagnetic transmitters, infrared emitting diodes, radar repeaters, etc.) may be attached to known instruments or objects that are used in a surgical field. The known instruments or objects may be, for example, bone mount accessories, retractors, clamps, and/or implants (e.g., screws, rods, interbody components of a known or estimated size, shape, and orientation). The navigation detectable aids and the known instruments or objects provide enough information about a position of the known instrument or object to plan a path that avoids the known instrument or object. The information about a position of the known instrument or object may include information about all degrees of freedom of the known instrument or object, or may include information about enough degrees of freedom to avoid the known instrument or object. For example, a symmetrically rotational tool will not require information about a rotation along its axis as it will not drastically change the path planning.

In such embodiments, an entire work volume may be mapped and one or more no-fly zones for a robot may be created. The navigation detectable aids, described above, detects a location of the known obstacles inside the general work volume. An obstacles map may be created based on navigation information and the known size and/or shape of the known instrument or object. A path may be planned for autonomous relevant motion of a robot, such that the robot will also avoid collision with the known instruments or objects. During motion, if a potential collision seems imminent (per the arm motion output and the constant navigation inputs), an alert and/or relevant actions may be taken (e.g., the robot may be stopped, the alert may be visual and/or audible, etc.).

The present disclosure enables path planning for autonomous movement of a robot. Further, the present disclosure also enables path planning for autonomously guiding a tool or an instrument on a path that enters a patient anatomy.

Embodiments of the present disclosure provide technical solutions to one or more of the problems of (1) autonomous movement of a robotic arm or a robot, (2) autonomous movement of a robotic arm or a robot that avoids collision with obstacles, (3) defining obstacles and/or no-fly zones in which a robotic arm or robot is restricted from contacting, and/or (4) defining or planning a path that starts outside of a patient anatomy and ends at least partially inside of a patient anatomy.

Turning first to FIG. 1, a block diagram of a system 100 according to at least one embodiment of the present disclosure is shown. The system 100 may be used to define or plan a path for a robotic arm and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200 and/or 300 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable image processing 120 and/or segmentation 122.

The image processing 120 enables the processor 104 to process image data of an image for the purpose of, for example, identifying information about one or more objects and/or anatomical elements depicted in the image. The information may comprise, for example, a pose of the one or more objects and/or anatomical elements, identification of the one or more objects and/or anatomical elements, identification of individual objects and/or anatomical elements, a boundary of the one or more objects and/or anatomical elements, etc. The image processing 120 may also enable the processor 104 to process the image data to convert the image data from two-dimensional image(s) to a three-dimensional representation.

The segmentation 122 enables the processor 104 to segment the image data so as to identify individual objects and/or anatomical elements in the image. The segmentation 122 may enable the processor 104 to identify a boundary of an object or an anatomical element by using, for example, feature recognition. In other instances, the segmentation 122 may enable the processor 104 to identify a boundary of an object or an anatomical element by determining a difference in or contrast between colors or grayscales of image pixels.

Content stored in the memory 106, if provided as instructions, may, in some embodiments, be organized into one or more applications, modules, packages, layers, or engines. Alternatively or additionally, the memory 106 may store other types of content or data (e.g., machine learning models, artificial neural networks, deep learning neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image objects, anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The image data received from the imaging device 112 may be processed by the processor 104 using the image processing 120. As previously described, the image data may be processed (which may use, for example, segmentation 122) to identify information about, for example, one or more objects and/or anatomical elements depicted in the image data. The identified information may be used to support the functionality of the robot 114. For example, the identified information may be used to determine one or more objects and/or anatomical elements to avoid by the robot 114. Similarly, the identified information may be use determine one or more target objects and/or anatomical elements for the robot 114.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

In the illustrated embodiment, the system 100 includes the controller 124, though in some embodiments the system 100 may not include the controller 124. The controller 124 may be an electronic, a mechanical, or an electro-mechanical controller. The controller 124 may comprise or may be any processor described herein. The controller 124 may comprise a memory storing instructions for executing any of the functions or methods described herein as being carried out by the controller 124. In some embodiments, the controller 124 may be configured to simply convert signals received from the computing device 102 (e.g., via a communication interface 108) into commands for operating robot 114 (and more specifically, for controlling one or more motors configured to move the robot 114), the navigation system 118, and/or the robot 114. In other embodiments, the controller 124 may be configured to process and/or convert signals received from the computing device 102, navigation system 118, and/or the robot 114. Further, the controller 124 may receive signals from one or more sources (e.g., computing device 102, the navigation system 118, and/or the robot 114) and may output signals to one or more sources.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 200 and/or 300 described herein. The system 100 or similar systems may also be used for other purposes.

Figure 2:
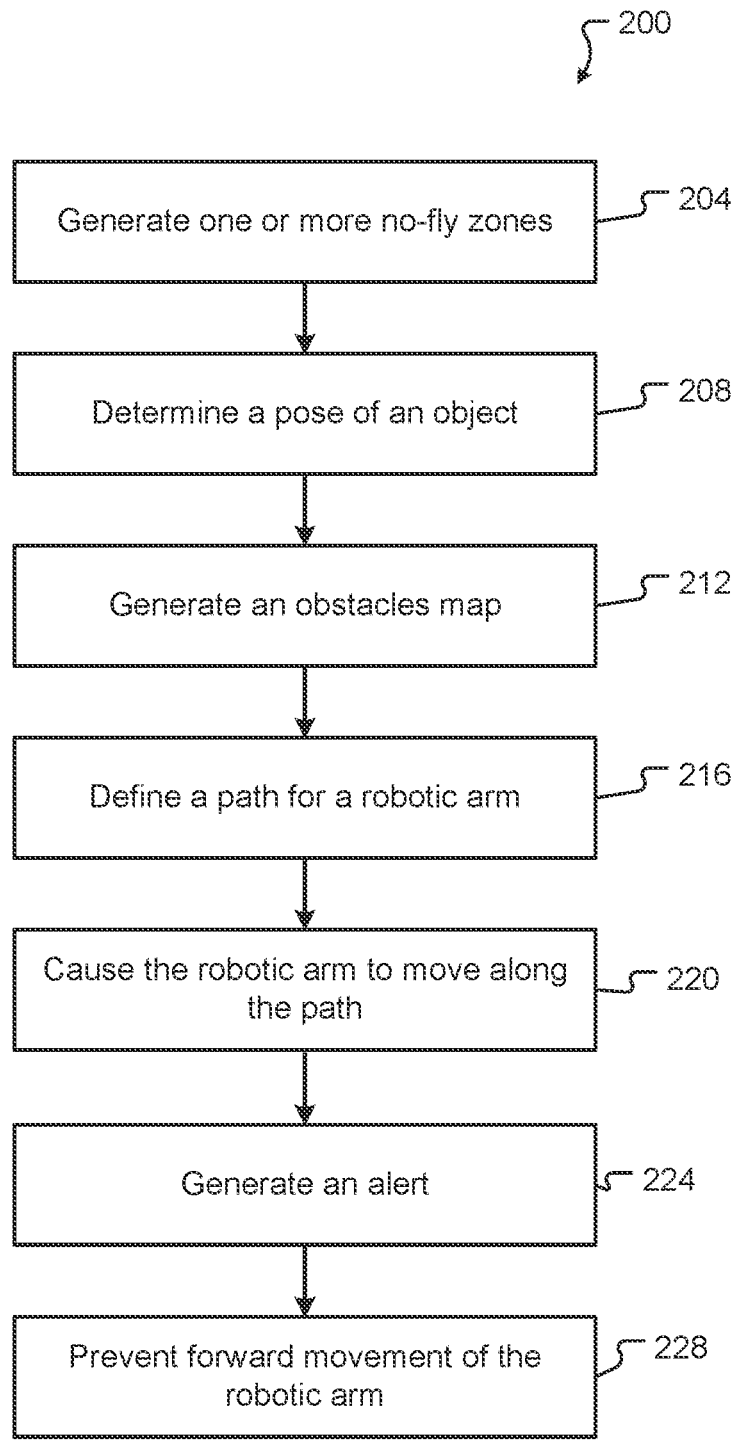
FIG. 2 is a flowchart according to at least one embodiment of the present disclosure.

FIG. 2 depicts a method 200 that may be used, for example, for defining a path for a robotic arm.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing elements stored in a memory such as the memory 106. The elements stored in the memory and executed by the processor may cause the processor to execute one or more steps of a function as shown in method 200. One or more portions of a method 200 may be performed by the processor executing any of the contents of memory, such as an image processing 120 and/or a segmentation 122.

The method 200 comprises generating one or more no-fly zones (step 204). The one or more no-fly zones may correspond to a section of a work volume defined as inaccessible or off limits to a robotic arm such as the robotic arm 116 and/or any portion of a robot such as the robot 114. The work volume defines a volume of space surrounding or in a patient in which the robotic arm may access. Though each of the one or more no-fly zones may define at least one volume in which the robotic arm and/or any portion of the robot is restricted from accessing, it will be appreciated that the robotic arm may be capable of accessing a no-fly zone, but is prevented from doing so by, for example, control signaling. In such instances, the robotic arm and/or any portion of the robot may be stopped at a boundary of each of the one or more no-fly zones using control signaling generated and/or transmitted by, for example, a controller such as the controller 124. The control signaling may, for example, cause one or more motors to stop movement of the robotic arm and/or the robot at the boundary of a no-fly zone. The control signaling may also cause the one or more motors to move the robotic arm and/or the robot away from the boundary of the no-fly zone. In some embodiments, the control signaling may prohibit the one or more motors from further moving the robotic arm and/or the robot. In some embodiments, the control signaling may prohibit certain motions of the one or more motors. In other examples, the control signaling may cause a brake to apply a braking force to the one or more motors to prevent movement of the robotic arm and/or the robot into the one or more no-fly zones.

In some embodiments, the work volume may be defined by defining a volume of the operating room and subtracting the one or more no-fly zones from the volume. The volume of the operating room may be determined by, for example, a processor such as the processor 104 based on information about the operating room. The information may be, for example, an image, sensor data, Lidar data, and/or electromagnetic data. In other instances, the volume of the operating room may be calculated from dimensions of the room. In other embodiments, the volume of the operating room and the one or more no-fly zones may be generated by scanning an operating room (using, for example, an imaging device) to determine one or more physical boundaries within the operating room and defining the one or more no-fly zones based on the one or more physical boundaries.

The one or more no-fly zones may be generated automatically by a processor such as the processor 104. In some embodiments, a 3D model may be generated based on the work volume and the one or more no-fly zones. In other embodiments, the work volume and/or the one or more no-fly zones may be or comprise, or be based on, surgeon input received via a user interface such as the user interface 110. In further embodiments, the work volume and/or no-fly zones may be mapped or generated automatically by the processor, and may thereafter be reviewed and approved (or modified) by a surgeon or other user.

The method 200 also comprises determining a pose of an object (step 208). The object may be an instrument such as, for example, a retractor, a tubular retractor, or a port, or may be any component used in a surgical operation, procedure, or step or any component that may be present in a surgical operating room including, for example, imaging devices, tables, operating personnel, or the like. It will be appreciated that a pose for any number of objects may be determined. For example, a pose of each of one or more retractors and/or one or more screws may be determined.

In some embodiments, the pose of the object may be received from a sensor, such as a position sensor. In other embodiments, the pose of the object may be received from the robotic arm orienting or supporting the object (for example, a retractor may be oriented by the robotic arm). In still other embodiments, the pose of the object may be received as input from a user such as, for example, a surgeon.

In other embodiments, the pose of the object may be received from a navigation camera of a navigation system such as the navigation system 118. In such embodiments, the object may include one or more markers (such as, for example, reference markers) detectable by the navigation system. Because the pose of the one or more markers correlates to the pose of the object, the pose of the object can be obtained from determining the pose of the one or more markers. The one or more markers may comprise infrared emitting devices, light emitting diodes, electromagnetic transmitters, radar repeaters, spheres, and/or reflective markers. In such embodiments image data depicting the one or more markers may be received and a pose of the one or more markers may be determined based on the image data. In such embodiments, the image data may be processed using instructions or models stored in the memory that, when executed, enable image processing such as image processing 120 of the image data to identify the one or more markers in the image data. In other instances, the image data may be processed using instructions or models stored in the memory that, when executed, enable segmentation such as segmentation 122 of the image data to identify the one or more markers in the image data.

The method 200 also comprises generating an obstacles map (step 212). The obstacles map may be based on the pose of the object determined in, for example, step 208 described above, and known dimensions of the object. It will be appreciated that in some embodiments the obstacles map includes more than one object. The dimensions may include a width, a length, a depth, a thickness, and/or a diameter of the object. The dimensions may also include relative dimensions of the object. For example, the dimensions may include a distance between two objects, such as, for example, a distance between two arms of a retractor. In some embodiments, the dimensions may be received as input from the user. In other embodiments, the dimensions may be received from a database such as the database 130. In still other embodiments, the dimensions may be measured preoperatively or intraoperatively by, for example, the user or the navigation system. For example, the dimensions of the object may be measured using a navigated probe, for example, that may be brought to contact different points of the object. The navigated points of the object may then be used to determine the dimensions of the object.

Generating the obstacles map may comprise defining a three-dimensional boundary of the object based on the known dimensions of the object. In some embodiments, the object may be positioned within the obstacles map and a surface representation may be formed based on the known dimensions of the object. In some embodiments, the surface representation may be a virtual mesh. The virtual mesh may comprise, for example, a set of polygonal faces that, when taken together, form a surface covering of a virtual object. The set of polygonal faces may be connected at their edges and vertices to define a shape of the virtual object.

The method 200 also comprises defining a path for a robotic arm (step 216). The path avoids collision with the object identified in the obstacles map generated in, for example, step 212 above and also avoids the one or more no-fly zones generated in, for example, step 204 above. The path is also disposed within the work volume. The path ensures that any portion of the robot avoids the one or more no-fly zones and the object(s) defined in the obstacles map. The path may extend from outside of a patient anatomy to within the patient anatomy. The path may also orient the robotic arm or any portion of the robot to a surgical site on a patient. For example, the surgical site may be an incision and the object may be two retractors positioned to retract and hold open the incision. The path may cause the robotic arm to orient to the incision while avoiding the no-fly zones and the two retractors. Further, in some embodiments, the robotic arm may orient a tool. The tool may be, for example, a knife, a drill, a screw, or the like. The path may cause the robotic arm to orient the tool from a first position outside of a patient anatomy to a second position inside of the patient anatomy. The second position may be, for example, a position inside of an incision on a patient. For example, the path may cause the robotic arm to orient a screw through the incision to, for example, a vertebra.

The method 200 also comprises causing the robotic arm to move along the path (step 224). In some embodiments, instructions to cause the robotic arm to move along the path may be generated by, for example, the processor and transmitted to the robotic arm (or a controller thereof). In other embodiments, instructions to orient the robotic arm at one or more poses may be generated by, for example, the processor and displayed on a user interface such as the user interface 110.

The method 200 also comprises generating an alert (step 224). The alert may be generated when a distance between the robotic arm or any portion of the robot and the object or a boundary of the one or more no-fly zones reaches or surpasses a threshold. The alert may be, for example, audible, visual, or a combination thereof. The alert, in some embodiments, may simply notify a user, such as a surgeon or other medical personnel, that the threshold has been met or exceeded.

The threshold may be based on an acceptable distance between the robotic arm or any portion of the robot and the object and/or a boundary of the one or more no-fly zones. Such distance between the robotic arm or any portion of the robot and the object and/or the boundary the one or more no-fly zones may be determined by, for example, monitoring a pose of the robotic arm or any portion of the robot and monitoring a pose of the object. The pose of the robotic arm or any portion of the robot may be monitored using, for example, sensors disposed or integrated with the robotic arm or any portion of the robot and/or may be monitored by the navigation system. The pose of the object may be monitored by, for example, the navigation system or a robotic arm orienting the object. In some embodiments, the distance may correlate to a difference between a pose of the robotic arm (or any portion of the robot) and a pose of the object and/or a difference between a pose of the robotic arm (or any portion of the robot) and a boundary of the one or more no-fly zones.

It will be appreciated that in some embodiments, the threshold may comprise multiple thresholds. For example, a threshold for a distance between the robotic arm (or any portion of the robot) and a retractor may be less than a threshold for a distance between the robotic arm (or any portion of the robot) and a table. In some embodiments, the threshold may be received as input from, for example, a user such as a surgeon or other medical provider or may be provided in a surgical plan. In other embodiments, the threshold may be determined automatically by, for example, the processor preoperatively or intraoperatively. For example, the processor may execute a model which receives an expected position of an object and/or a path for a robotic arm as input and output one or more thresholds. The model may be trained using, for example, historical thresholds, historical objects, and/or one or more historical paths.

It will be appreciated that in some embodiments, the method 200 may not include the step 224.

The method 200 also comprises preventing forward movement of the robotic arm (step 228). The forward movement of the robotic arm or any portion of the robot may be prevented when a distance between the robotic arm or any portion of the robot and the object and/or a distance between the robotic arm or any portion of the robot and a boundary of the one or more no-fly zones reaches or surpasses a threshold. The threshold may be the same as or similar to the threshold describe above in step 224. Forward movement of the robotic arm may be prevented by, for example, control signaling generated by, for example, the controller. As previously described, in such instances, the robotic arm and/or any portion of the robot may be stopped at the one or more no-fly zones or the object using control signaling when a distance between the robotic arm or any portion of the robot and the object or the boundary of the one or more no-fly zones meets or exceeds the threshold. The control signaling may, for example, cause one or more motors to stop movement of the robotic arm and/or the robot. The control signaling may also cause the one or more motors to move the robotic arm and/or the robot away from the no-fly zone or the object. In other examples, the control signaling may cause a brake to apply a braking force to the one or more motors to prevent movement of the robotic arm and/or the robot.

It will be appreciated that in some embodiments, the method 200 may not include the step 228. In still other embodiments, the steps 224 and 228 may be combined. For example, when a distance between the robotic arm or any portion of the robot and the object or the boundary the one or more no-fly zones meets or exceeds a threshold, then both an alert may be generated and the robotic arm or any portion of the robot may be prevented from moving forward along the path.

It will also be appreciated that in some embodiments, step 220 may be reestablished when steps 224 and/or 228 are completed. For example, in embodiments where the control signaling causes the robotic arm or any portion of the robot to move away from the no-fly zone and/or the object, the control signaling may cause the robotic arm to resume movement along the path when the distance between the robotic arm and/or any portion of the robot and the no-fly zone and/or object no longer meets or exceeds the threshold. In some embodiments, the robotic arm may pause while the path is updated (using, for example, method 300 described below), then resume movement along an updated path. In still other embodiments, the robotic arm may not resume movement until a user such as a surgeon or other medical provider enables movement of the robotic arm. For example, the user may receive an alert (which may be generated in, for example, step 224) and the robotic arm may not resume movement until the user has acknowledge the alert via, for example, the user interface.

The present disclosure encompasses embodiments of the method 200 that comprise more or fewer steps than those described above, and/or one or more steps that are different than the steps described above.

Figure 3:
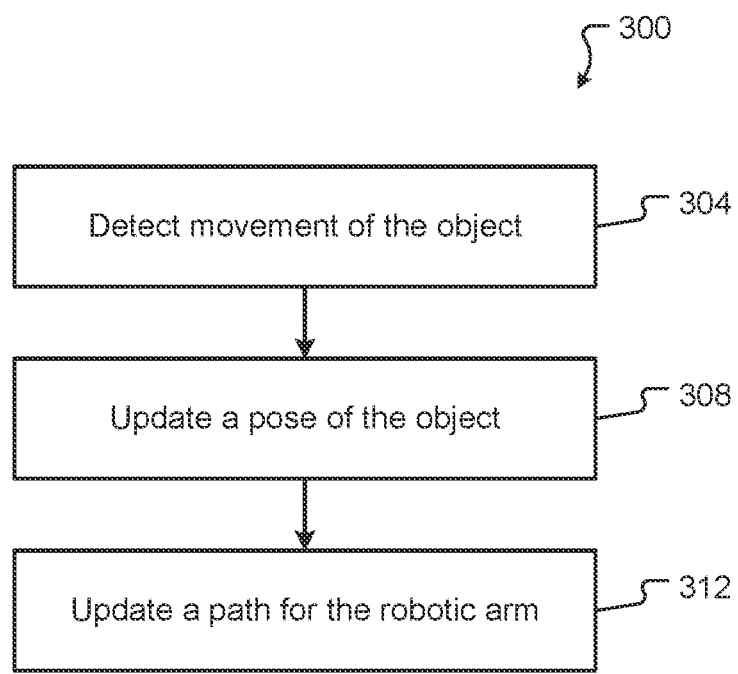
FIG. 3 is a flowchart according to at least one embodiment of the present disclosure.

FIG. 3 depicts a method 300 that may be used, for example, for updating a path for a robotic arm.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing elements stored in a memory such as the memory 106. The elements stored in memory and executed by the processor may cause the processor to execute one or more steps of a function as shown in method 300. One or more portions of a method 300 may be performed by the processor executing any of the contents of memory, such as an image processing 120 and/or a segmentation 122.

The method 300 comprises detecting movement of an object (step 304). Detecting movement of the object may comprise comparing a first pose of an object and a second pose of the object. Obtaining or determining the first pose and the second pose may be the same as or similar to the step 208. The second pose of the object may be obtained after the first pose.

In other embodiments, detecting movement of the object may comprise comparing a first image of the object (which may be received from, for example, an imaging device such as the imaging device 112) and a second image of the object. More specifically, a pose of the object in the first image may be compared to a pose of the object in the second image. Movement may be detected when a difference between the first pose and the second pose (whether obtained from images, sensor data, navigation data, or otherwise) meets or exceeds a movement threshold.

The movement threshold may be based on an acceptable amount of movement that the object may exhibit. In some instances, no movement may be desired, however, a small movement threshold may be acceptable. In other instances, the object may be expected to move due to, for example, a surgical step. As such, the movement threshold may be based on an acceptable difference between an actual movement and a predicted movement of the object. More specifically, a difference between an actual position of the object after the predicted movement and an expected position of the object may be determined to meet or exceed the movement threshold.

In some embodiments, the movement threshold may be received as input from, for example, a user such as a surgeon or other medical provider or may be provided in a surgical plan. In other embodiments, the movement threshold may be determined automatically by, for example, the processor preoperatively or intraoperatively. For example, the processor may execute a model which receives an expected position of the object and/or a predicted movement of the object as input and output one or more movement thresholds. The model may be trained using, for example, historical movement thresholds, historical objects, and/or one or more historical predicted movements of historical objects.

The method 300 also comprises updating a pose of the object (step 308). The pose of the object may be updated in an obstacles map based on the detected movement. The obstacles map may be generated, for example, in step 212 of method 200 described above. Updating the pose of the object in the obstacles map may comprise moving a three-dimensional boundary of the object to reflect the update pose of the object. In other instances, updating the pose of the object in the obstacles map may comprise regenerating the three-dimensional boundary of the object to reflect the updated pose of the object.

The method 300 also comprises updating a path for a robotic arm (step 312). Updating the path for the robotic arm may be based on the updated pose of the object. In other words, the path may be updated to avoid the object after the object has moved. In some embodiments, updating the path for the robotic arm updates the entire path for the robotic arm. In other embodiments, updating the path for the robotic arm updates a remaining portion of the path for the robotic arm. Further, in some embodiments, the step 312 comprises repeating the steps 204 and 212 of method 200 described above. In other words, the one or more no-fly zones may be re-generated (step 204) and/or the obstacles map may be regenerated (step 212) based on the updated pose of the object. In such embodiments, the path may be updated based on the regenerated one or more no-fly zones and/or the regenerated obstacles map.

It will be appreciated that the steps 302, 308, 312 may be repeated continuously, at a time increment, and/or when a surgical step has occurred. For example, the steps 302, 308, 312 may be repeated any time movement of the object is detected, after a surgical step has been executed, or otherwise.

The present disclosure encompasses embodiments of the method 300 that comprise more or fewer steps than those described above, and/or one or more steps that are different than the steps described above.

As noted above, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for defining a path for a robotic arm, the system comprising:
   a robotic arm;
   an object;
   a tool oriented by the robotic arm;
   a processor; and
   a memory storing data for processing by the processor, the data, when processed, causing the processor to:
      scan an operating room to determine one or more physical boundaries within the operating room;
      generate one or more no-fly zones based on the physical boundaries within the operating room, wherein the one or more no-fly zones correspond to a section of a work volume defined as inaccessible to the robotic arm, wherein the work volume is defined as accessible to the robotic arm;
      determine a pose of the object;
      generate an obstacles map based on the determined pose and known dimensions of the object; and
      define a path for the robotic arm to orient along within the operating room, the path avoiding collision with the object identified in the obstacles map and avoiding the one or more no-fly zones,
      wherein the path orients the tool from a first position outside of a patient and within the operating room to a second position inside of the patient.

2. The system of claim 1, wherein the path orients the robotic arm to a surgical site on the patient.

3. The system of claim 1, wherein the memory stores further data for processing by the processor that, when processed, causes the processor to:
   generate an alert when a distance between the robotic arm and the object reaches a threshold.

4. The system of claim 1, wherein the memory stores further data for processing by the processor that, when processed, causes the processor to:
   prevent forward movement of the robotic arm on the path when a distance between the robotic arm and the object reaches a threshold.

5. The system of claim 1, wherein the object is positioned at least partially inside of the patient.

6. The system of claim 1, further comprising one or more markers disposed on the object.

7. The system of claim 6, wherein the one or more markers are at least one of infrared emitting devices, light emitting diodes, electromagnetic transmitters, radar repeaters, spheres, or reflective markers.

8. The system of claim 6, wherein determining the pose of the object comprises:
   receiving image data depicting the one or more markers; and
   determining a pose of the one or more markers based on the image data, the pose of the one or more markers correlating to the pose of the object.

9. The system of claim 6, further comprising a navigation system configured to track a pose of each of the one or more markers, and wherein determining the pose of the object uses the navigation system.

10. The system of claim 1, wherein generating the obstacles map comprises defining a three-dimensional boundary of the object based on the known dimensions of the object.

11. The system of claim 1, wherein the memory stores further data for processing by the processor that, when processed, causes the processor to:
   detect movement of the object;
   update the pose of the object in the obstacles map based on the detected movement; and
   update the path for the robotic arm based on the updated pose of the object.

12. A device for defining a path for a robotic arm, the device comprising:
   a tool oriented by the robotic arm;
   a processor; and
   a memory storing data for processing by the processor, the data, when processed, causing the processor to:
      scan an operating room to determine one or more physical boundaries within the operating room;
      generate one or more no-fly zones based on the physical boundaries within the operating room, wherein the one or more no-fly zones correspond to a section of a work volume defined as inaccessible to a robotic arm, wherein the work volume is defined as accessible to the robotic arm;

determine a pose of object;

generate an obstacles map based on the determined pose and known dimensions of the object; and define a path for the robotic arm to orient along within the operating room, the path avoiding collision with the object identified in the obstacles map and avoiding the one or more no-fly zones, wherein the path orients the tool from a first position outside of a patient and within the operating room to a second position inside of the patient.

13. The device of claim 12, wherein the memory stores further data for processing by the processor that, when processed, causes the processor to:

generate an alert when a distance between the robotic arm and the object reaches a threshold.

14. The device of claim 12, wherein the memory stores further data for processing by the processor that, when processed, causes the processor to:

prevent forward movement of the robotic arm on the path when a distance between the robotic arm and the object reaches a threshold.

15. The device of claim 12, wherein generating the obstacles map comprises defining a three-dimensional boundary of the object based on the known dimensions of the object.

16. The device of claim 12, wherein determining the pose of the object comprises receiving image data depicting one or more markers disposed on the object and determining a pose of the one or more markers based on the image data, the pose of the one or more markers correlating to the pose of the object.

17. A system for defining a path for a robotic arm comprising:

a robotic arm;

an object;

a tool oriented by the robotic arm;

one or more markers disposed on the object;

a navigation system configured to track a pose of each of the one or more markers;

a processor; and a memory storing data for processing by the processor, the data, when processed, causes the processor to:

scan an operating room to determine one or more physical boundaries within the operating room;

generate one or more no-fly zones based on the physical boundaries within the operating room, wherein the one or more no-fly zones correspond to a section of a work volume defined as inaccessible to the robotic arm, wherein the work volume is defined as accessible to the robotic arm;

determine a pose of the one or more markers using the navigation system;

generate an obstacles map based on the determined pose of the one or more markers and known dimensions of the object; and define a path for the robotic arm to orient along within the operating room, the path avoiding collision with the object identified in the obstacles map and avoiding the one or more no-fly zones, wherein the path orients the tool from a first position outside of a patient and within the operating room to a second position inside of the patient.

* * * * *